United States Patent [19]
Everhart et al.

[11] Patent Number: 6,060,256
[45] Date of Patent: *May 9, 2000

[54] OPTICAL DIFFRACTION BIOSENSOR

[75] Inventors: Dennis S. Everhart, Alpharetta; Mark L. Jones, Atlanta; Rosann Marie Kaylor, Cumming, all of Ga.

[73] Assignee: Kimberly-Clark Worldwide, Inc., Neenah, Wis.

[*] Notice: This patent is subject to a terminal disclaimer.

[21] Appl. No.: 08/991,644

[22] Filed: Dec. 16, 1997

[51] Int. Cl.$^7$ ...................... G01N 33/567; G01N 33/566; G01N 33/48; G01N 21/00
[52] U.S. Cl. .................. 435/7.21; 435/7.2; 436/501; 436/513; 436/63; 436/164; 427/2.13
[58] Field of Search .................................. 427/2.13, 2.24, 427/2.3, 337, 388.1, 387, 405, 552; 435/7.21, 7.2, 291; 436/501, 513, 63, 164

[56] References Cited

U.S. PATENT DOCUMENTS

| | | |
|---|---|---|
| 4,312,228 | 1/1982 | Wohltjen . |
| 4,363,874 | 12/1982 | Greenquist . |
| 4,399,686 | 8/1983 | Kindlund et al. . |
| 4,416,505 | 11/1983 | Dickson . |
| 4,534,356 | 8/1985 | Papadakis . |
| 4,561,286 | 12/1985 | Sekler et al. . |
| 4,562,157 | 12/1985 | Lowe et al. . |
| 4,596,697 | 6/1986 | Ballato . |
| 4,661,235 | 4/1987 | Krull et al. . |
| 4,690,715 | 9/1987 | Allara et al. . |
| 4,776,944 | 10/1988 | Janata et al. . |
| 4,812,221 | 3/1989 | Madou et al. . |
| 4,837,715 | 6/1989 | Ungpiyakul et al. . |
| 4,842,783 | 6/1989 | Blaylock . |
| 4,844,613 | 7/1989 | Batchelder et al. . |
| 4,851,816 | 7/1989 | Macias et al. . |
| 4,877,747 | 10/1989 | Stewart . |
| 4,895,017 | 1/1990 | Pyke et al. . |
| 4,992,385 | 2/1991 | Godfrey . |
| 5,023,053 | 6/1991 | Finlan . |
| 5,035,863 | 7/1991 | Finlan et al. . |
| 5,055,265 | 10/1991 | Finlan . |
| 5,057,560 | 10/1991 | Mueller . |
| 5,063,081 | 11/1991 | Cozzette et al. . |
| 5,064,619 | 11/1991 | Finlan . |
| 5,076,094 | 12/1991 | Frye et al. . |
| 5,096,671 | 3/1992 | Kane et al. . |
| 5,114,676 | 5/1992 | Leiner et al. . |
| 5,134,057 | 7/1992 | Kuypers et al. . |
| 5,143,854 | 9/1992 | Perrung et al. . |
| 5,152,758 | 10/1992 | Kaetsu et al. . |
| 5,182,135 | 1/1993 | Giesecke et al. . |
| 5,189,902 | 3/1993 | Groeninger . |
| 5,190,350 | 3/1993 | Backman . |
| 5,235,238 | 8/1993 | Nomura et al. . |
| 5,242,828 | 9/1993 | Bergstrom et al. . |
| 5,268,306 | 12/1993 | Berger . |
| 5,280,548 | 1/1994 | Atwater et al. . |
| 5,304,293 | 4/1994 | Tierney et al. . |
| 5,327,225 | 7/1994 | Bender et al. . |
| 5,334,303 | 8/1994 | Muramatsu et al. . |
| 5,369,717 | 11/1994 | Attridge . |
| 5,374,563 | 12/1994 | Maule . |
| 5,376,255 | 12/1994 | Gumbrecht et al. . |
| 5,402,075 | 3/1995 | Lu et al. . |
| 5,404,756 | 4/1995 | Briggs et al. . |
| 5,415,842 | 5/1995 | Maule . |
| 5,418,136 | 5/1995 | Blessing et al. . |
| 5,430,815 | 7/1995 | Shen et al. . |
| 5,436,161 | 7/1995 | Bergstrom et al. . |
| 5,451,683 | 9/1995 | Barrett et al. . |
| 5,455,475 | 10/1995 | Josse et al. . |
| 5,482,830 | 1/1996 | Bogart et al. . |
| 5,482,867 | 1/1996 | Barrett et al. . |
| 5,489,678 | 2/1996 | Fodor et al. . |
| 5,489,988 | 2/1996 | Ackley et al. . |
| 5,492,840 | 2/1996 | Malmqvist et al. . |
| 5,510,481 | 4/1996 | Bednarski . |
| 5,512,131 | 4/1996 | Kumar et al. . |
| 5,514,559 | 5/1996 | Markert-Hahn et al. . |
| 5,527,711 | 6/1996 | Tom-Moy et al. . |
| 5,554,541 | 9/1996 | Malmqvist et al. . |
| 5,568,606 | 10/1996 | Bogart et al. . |
| 5,620,850 | 4/1997 | Bamdad et al. . |
| 5,643,681 | 7/1997 | Voorhees et al. . |
| 5,658,443 | 8/1997 | Yamamoto et al. . |
| 5,830,539 | 11/1998 | Yan et al. ................................ 427/551 |

FOREIGN PATENT DOCUMENTS

| | | |
|---|---|---|
| 0 453 820 | 10/1991 | European Pat. Off. . |
| 0453820 | 10/1991 | European Pat. Off. . |
| 0 657 73 | 6/1995 | European Pat. Off. . |
| 2273772 | 6/1994 | United Kingdom . |
| 90/05305 | 5/1990 | WIPO . |
| 91/05999 | 5/1991 | WIPO . |
| 96/26435 | 8/1996 | WIPO . |
| WO 96/26435 | 8/1996 | WIPO . |
| 96/29629 | 9/1996 | WIPO . |
| 9633971 | 10/1996 | WIPO . |

OTHER PUBLICATIONS

Abbott et al., Using Micromachining, Molecular Self–Assembly, and Wet Etching to Fabricate 0.1–1 $\mu$m– Scale Structures of Gold and Silicon, Chemistry of Materials, 6, No. 5, pp. 596–602 (1994).

Burton et al. "Prediction of Segregation to Alloy Surfaces from Bulk Phase Diagram", Phys. Rev. Letter, vol. 37, No. 21, pp. 1433–1436 (Nov. 22, 1976).

(List continued on next page.)

Primary Examiner—Keith D. MacMillan
Assistant Examiner—P. Ponnaluri
Attorney, Agent, or Firm—Jones & Askew, LLP

[57] ABSTRACT

The present invention provides an inexpensive and sensitive device and method for detecting and quantifying analytes present in a medium. The device comprises a metalized film upon which is printed a specific, predetermined pattern of analyte-specific receptors. Upon attachment of a target analyte to select areas of the plastic film upon which the receptor is printed, diffraction of transmitted and/or reflected light occurs via the physical dimensions and defined, precise placement of the analyte. A diffraction image is produced which can be easily seen with the eye or, optionally, with a sensing device.

29 Claims, 6 Drawing Sheets

OTHER PUBLICATIONS

Daphint et al., "Probing of strong and weak electrolytes with acoustic wave fields", Sensors and Actuators B, vol. 9, pp. 155–162 (1992).

Folkers et al., "Self–Assembled Monolayers of Long–Chain Hydroxamic Acids on the Native Oxides of Metals", Langmuire, vol. 11, No. 3, pp. 813–824 (1995).

Irie, M. "Stimuli–Responsive Poly(N–isopropylacrylamide) Photo– and Chemical–Induced Phase Transitions", Advances in Polymer Science, vol. 110, pp. 49–65 (1993).

Jeon et al., "Patterned Self–Assembled Monolayers Formed by Microcontact Printing Direct Selective Metalization by Chemical Vapor Deposition on Planar and Nonplanar Substrates", Langmuir, vol. 11, No. 8, pp. 3024–3026 (1995).

Johnson et al. "Orientation dependence of surface segregation in a dilute Ni–Au alloy", J. Vac. Sci. Technol., vol. 15, No. 2, pp. 467–469 (Mar./Apr. 1978).

Josse et al., "Electrical Surface Perturbation of a Piezoelectric Acoustic Plate Mode by a Conductive Liquid Loading", IEEE Transactions on Ultrasonics, Ferroelectrics, and Frequency Control, vol. 39, No. 4, (Jul. 1992).

"Mechanical resonance gas sensors with piezoelectric excitation and detection using PVDF polymer foils" by R. Block et al., Sensors and Actuators, vol. B7, Mar. 1992, pp. 596–601.

"Sensing liquid properties with thickness–shear mode resonators" by S.J. Martin, Sensors and Actuators A. vol. A44, Sep. 1994, pp. 209–218.

Responsive Gels: Volume Transitions I, vol. 109: Advances in Polymer Science, Dusek, K. ed., Springer–Verlag, Berlin, 1993.

Responsive Gels: Volume Transitions II, vol. 110: Advances in Polymer Science, Dusek, K. ed., Springer–Verlag, Berlin, 1993.

Muller, W. et al., Science, vol. 262, Dec. 10, 1993, pp. 1706–1708.

Jennane, J. et al. Can. J. Chem. vol. 74, 1996, pp. 2509–2517.

Diamandis, EP et al., *Clin. Chem.*, vol. 37(5), 1991, pp. 625–633.

Bhatia, S.K. et al., 1992, *J. Am. Chem. Soc.*, vol. 114, p. 4432.

Phatia, S.K. et al., Analytical Biochem., vol. 208, pp. 197–205, 1993.

Häussling, L. et al., Angew, Chem., Int. Ed. Engl., vol. 30, No. 5, 1991, pp. 569–572.

Larsen N.B. et al., "Order in Microcontact Printed Self–Assembled Monolayers", *J. Am. Chem. Soc.* vol. 119, pp. 3017–3026, 1997.

Josse et al., "On the use of ZX–LiNbO3 acoustic plate mode devices as detectors for dilute electrolytes", Sensors and Actuators B, vol. 9, pp. 97–112 (1992).

Kelkar et al., "Acoustic Plate Waves for Measurement of Electrical Properties of Liquids", Microchem. Journal, vol. 43, pp. 155–164 (1991).

Kim et al., "Combining Patterned Self–Assembled Monolayers of Alkanethiolates on Gold with Anisotropic Etching of Silicon to Generate Controlled Surface Morphologies", J. Electrochem. Soc., vol. 142, No. 2, pp. 628–633 (Feb. 1995).

Kokufuta, E. "Novel Applications for Stimulus–Sensitive Polymer Gels in the Preparation of Functional Immobilized Biocatalysts", Advances in Polymer Science, vol. 110, pp. 157–177 (1993).

Kumar et al., "Features of gold having micrometer to centimeter dimensions can be formed through a combination of stamping with an elastomeric stamp and an alkanethiol "ink" following by chemical etching", Appl. Phys. Lett., vol. 63, pp. 2002–2004 (1993).

Kumar et al., "Paterened Condensation Figures as Optical Diffraction Gratings", Science, vol. 263, pp. 60–62 (Jan. 7, 1994).

Kumar et al., "Patterning Self–Assembled Monolayers: Applications in Materials Science", Langmuir, vol. 10, pp. 1498–1511 (1994).

Liedberg et al, "Molecular Gradients of ω–Substituted Alkanethiols on Gold: Preparation and Characterization", Langmuir, vol. 11, pp. 3821–3827 (1995).

Mrksich et al., "Patterning self–assembled monolayers using microcontact printing: A new technology for biosensors?", Tibtech, vol. 13, pp. 228–235 (1995).

Okano, t. "Molecular Design of Temperature–Responsive Polymers as Intelligent Materials", Advances in Polymer Science, vol. 110, pp. 179–197 (1993).

Osada et al, "Stimuli–Responsive Polymer Gels and Their Application to Chemomechanical Systems", Prog. Polym. Sci., vol. 18, pp. 187–226 (1993).

Osada et al., "Intelligent Gels", Scientific American, pp. 82–87, May 1993.

Saito et al., "Volume Phase Transition of N–Alkylacrylamide Gels", Advances on Polymer Science, vol. 109, pp. 207–232 (1993).

Seah, M.P. "Quantitative Prediction of Surface Segregation", Journal of Catalysis, vol. 57, pp. 450–457 (1979).

Shana et al, "Analysis of electrical equivalent circuit of quartz crystal resonator loaded with viscous conductive liquids", Journal of Electroanalytical Chemistry, vol. 379, pp. 21–33 (1994).

Shana et al., "Quartz Crystal Resonators as Sensors in Liquids Using the Acoustoelectric Effect", Anal. Chem., vol. 66, pp. 1955–1964 (1994).

Shibayama et al., "Volume Phase Transition and Related Phenomena of Polymer Gels", Advances in Polymer Science, vol. 109, pp. 1–62 (1993).

Tsai et al., "Comment on the Prediction of Segregation to Alloy Surfaces", Journal of Catalysis—Letters to the Editor, vol. 50, pp. 200–202 (1977).

Wilbur et al., "Microfabrication by Microcontact Printing of Self–Assembled Monolayers", Adv. Mater., vol. 6, No. 7/8, pp. 600–604 (1994).

OPTICAL DIFFRACTION BIOSENSOR

TECHNICAL FIELD

The present invention is in the field of analyte sensors and, more specifically the present invention is in the field of microcontact printing binders on metal films to produce optical diffraction biosensors.

BACKGROUND OF THE INVENTION

Microcontact printing is a technique for forming patterns of organic monolayers with micron and submicron lateral dimensions. It offers experimental simplicity and flexibility in forming certain types of patterns. In the prior art, microcontact printing was used with self-assembled monolayers of long-chain alkanethiolates to form organic structures on gold and other metals. These patterns acted as nanometer resists by protecting the supporting metal from corrosion by appropriately formulated etchants, or, allowed for the selective placement of fluids on hydrophilic regions of the pattern. In general, patterns of self-assembled monolayers having dimensions that can be less than 1 micron are formed by using the alkanethiol as an "ink", and by printing them on the metal support using an elastomeric "stamp". The stamp is fabricated by molding a silicone elastomer using a master prepared by optical or X-ray microlithography or by other techniques. (See U.S. patent application Ser. Nos. 08/654,993; 08/769,594; 08/821,464; 08/707,456 and 08/768,449 which are incorporated herein in their entirety by reference)

Microcontact printing brings to microfabrication a number of new capabilities. Microcontact printing makes it possible to form patterns that are distinguished only by their constituent functional groups; this capability permits the control of surface properties such as interfacial free energies with great precision. In the prior art microcontact printing relies on molecular self-assembly. Using self-assembling monolayers, a system is generated that is (at least locally) close to a thermodynamic minimum and is intrinsically defect-rejecting and self-healing. Simple procedures, with minimal protection against surface contamination by adsorbed materials or by particles, can lead to surprisingly low levels of defects in the final structures. The procedure using self-assembling monolayers can be conducted at atmospheric pressure, in an unprotected laboratory atmosphere. Thus, microcontact printing that uses self-assembling monolayers is useful in laboratories that do not have routine access to the equipment normally used in microfabrication, or for which the capital cost of equipment is a serious concern. The patterned self-assembled monolayers can be designed to act as resists with a number of wet-chemical etchants.

Also in the prior art, a gold film 5 to 2000 nanometers thick is typically supported on a titanium-primed $Si/SiO_2$ wafer or glass sheet. The titanium serves as an adhesion promoter between gold and the support. However, the silicon wafer is rigid, brittle, and cannot transmit light. These silicon wafers are also not suitable for a large-scale, continuous printing process, such as in letterpress, gravure, offset, and screen printing (see *Printing Fundamentals*, A. Glassman, Ed. (Tappi Press Atlanta, Ga. 1981); *Encyclopedia Britannica*, vol. 26, pp. 76–92, 110–111 (Encyclopedia Brittanica, Inc. 1991)). In addition, silicon must be treated in a separate step with an adhesion promoter such as Cr or Ti, or Au will not adequately adhere, preventing formation of a stable and well-ordered monolayer. Finally, silicon is opaque to visible light, so any diffraction pattern obtained must be created with reflected, not transmitted light.

What is needed is an easy, efficient and simple method of contact printing a patterned receptor on an optically transparent, flexible substrate, that is amenable to continuous processing and does not use self-assembling monolayers. Such a method and the device resulting from such a method is simpler, not restricted to the limitations of self-assembling monolayers and is easier to manufacture.

SUMMARY OF THE INVENTION

The present invention provides an inexpensive and sensitive device and method for detecting and quantifying analytes present in a medium. The device comprises a metalized film upon which is printed a specific predetermined pattern of analyte-specific receptor. The present invention does not utilize self-assembling monolayers but is more general in that any receptor which can be chemically coupled to a surface can be used. Upon attachment of a target analyte which is capable of scattering light to select areas of the plastic film upon which the receptor is printed, diffraction of transmitted and/or reflected light occurs via the physical dimensions, refractive index and defined, precise placement of the analyte. In the case where an analyte does not scatter visible light because the analyte is too small or does not have an appreciable refractive index difference compared to the surrounding medium, the attachment of polymer beads coupled with the analyte to receptors is another method of producing diffraction of light. A diffraction image is produced which can be easily seen with the eye or, optionally, with a sensing device. The present invention is a biosensor comprising a polymer film coated with metal and a receptor layer printed onto the polymer film wherein the receptor layer has a receptive material thereon that specifically binds an analyte.

The present invention utilizes methods of contact printing of patterned monolayers utilizing derivatives of binders for microorganisms. One example of such a derivative is a thiol. The desired binders can be thiolated antibodies or antibody fragments, proteins, nucleic acids, sugars, carbohydrates, or any other functionality capable of binding an analyte. The derivatives are chemisorbed to metal surfaces such as metalized polymer films.

Patterned monolayers allow for the controlled placement of analytes thereon via the patterns of analyte-specific receptors. The biosensing devices of the present invention produced thereby are used by first exposing the biosensing device to a medium that contains the analyte of choice and then, after an appropriate incubation period, transmitting light, such as from a laser or a point light source, through the film. If the analyte is present in the medium and is bound to the receptors on the patterned monolayer, the light is diffracted in such a way as to produce a visible or near infrared image. In other words, the patterned monolayers with the analyte bound thereto can produce optical diffraction patterns which differ depending on the reaction of the receptors on the monolayer with the analyte of interest. The light can be in the visible spectrum, and be either reflected from the film, or transmitted through it, and the analyte can be any compound or particle reacting with the monolayer. The light can be a white light or monochromatic electromagnetic radiation in preferably the visible region. The present invention also provides a flexible support for a monolayer on gold or other suitable metal or metal alloy.

The present invention includes a support for a thin layer of gold or other suitable material which does not require an adhesion promoter for the formation of a well-ordered monolayer or thin layer of binder. The present invention also provides a support for a layer of gold or other material which is suitable for continuous printing, rather than batch, fabrication. In addition, the present invention provides a low-cost, disposable biosensor which can be mass produced. The biosensors of the present invention can be produced as a single test for detecting an analyte or it can be formatted as a multiple test device. The uses for the biosensors of the present invention include, but are not limited to, detection of chemical or biological contamination in garments, such as diapers, generally the detection of contamination by microorganisms in prepacked foods such as fruit juices or other beverages and the use of the biosensors of the present invention in health diagnostic applications such as diagnostic kits for the detection of antigens, microorganisms, and blood constituents.

In another embodiment of the present invention, nutrients for a specific class of microorganisms can be incorporated into the receptor monolayer. In this way, very low concentrations of microorganisms can be detected by first contacting the biosensor of the present invention with the nutrients incorporated therein and then incubating the biosensor under conditions appropriate for the growth of the bound microorganism. The microorganism is allowed to grow until there are enough organisms to form a diffraction pattern.

The present invention can also be used on contact lenses, eyeglasses, window panes, pharmaceutical vials, solvent containers, water bottles, bandaids, and the like to detect contamination.

These and other features and advantages of the present invention will become apparent after a review of the following detailed description of the disclosed embodiments.

DETAILED DESCRIPTION

Figure 1:
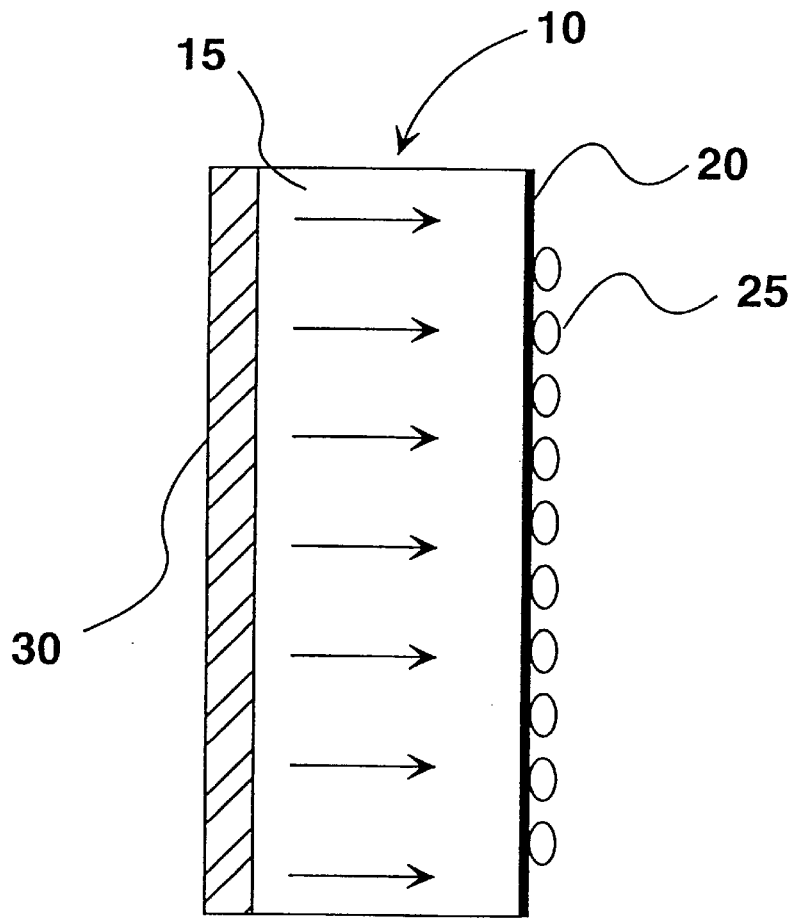
FIG. 1 is a schematic representation of a metal plated MYLAR film with a nutrient backing.

The present invention features improved biosensing devices, and methods for using such biosensing devices, for detecting and quantifying the presence or amount of an analyte of interest within a medium. The analytes that can be detected by the present invention include, but are not limited to, microorganisms such as bacteria, yeasts, fungi and viruses. In contrast to prior devices, those of the present invention allow detection of extremely small quantities of analyte in a medium in a rapid assay lasting only a few minutes. In addition, other than a light source, no signaling or associated electronic components are required in the biosensing devices of the present invention.

The present invention comprises micro-contact printing of analyte-specific receptors (thiolated binders) onto metalized plastic film which allows for the development of single use, disposable biosensors based on light diffraction to indicate the presence of the analyte. Upon attachment of a target analyte to select areas of the plastic film which contain the receptor, diffraction of transmitted and/or reflected light occurs via the physical dimensions and defined, precise placement of the analyte. For example, yeast, fungi or bacterium are large enough to act as diffraction elements for visible light when placed in organized patterns on a surface.

In addition to producing a simple diffraction image, patterns of analytes can be such as to allow for the development of a holographic sensing image and/or a change in visible color. Thus, the appearance of a hologram or a change in an existing hologram will indicate a positive response. The pattern made by the diffraction of the transmitted light can be any shape including, but not limited to, the transformation of a pattern from one pattern to another upon binding of the analyte to the receptive material. In particularly preferred embodiments, the diffraction pattern becomes discernible in less than one hour after contact of the analyte with the biosensing device of the present invention.

The diffraction grating which produces the diffraction of light upon interaction with the analyte must have a minimum periodicity of about ½ the wavelength and real or imaginary a refractive index different from that of the surrounding medium. Very small analytes, such as viruses or molecules, can be detected indirectly by using a larger particle that is specific for the small analyte. One embodiment in which the small analyte can be detected comprises coating the particle, such as a latex bead or polystyrene bead, with a receptive material, such as an antibody, that specifically binds to the analyte of interest. Particles that can be used in the present invention include, but are not limited to, glass, cellulose, synthetic polymers or plastics, latex, polystyrene, polycarbonate, proteins, bacterial or fungal cells and the like. The particles are desirably spherical in shape, but the structural and spatial configuration of the particles is not critical to the present invention. For instance, the particles could be slivers, ellipsoids, cubes, random shape and the like. A desirable particle size ranges from a diameter of approximately 0.2 $\mu$m to 50 $\mu$m, desirably between approximately 0.4 $\mu$m to 1 $\mu$m. The composition of the particle is not critical to the present invention.

It is to be understood that the optimal particle size is a function of the refractive index of the particle and the refractive index of the surrounding medium. A method of analyzing the optimal particle size for use in the present invention with a transmission image is by employing the equation;

$$t_{opt} = \lambda/2(n_2 - n_1)$$

wherein $t_{opt}$ = optimum height of the particle $\lambda$ = wavelength of incoming light $n_2$ = refractive index of particle $n_1$ = refractive index of surrounding medium For a reflection image, the optimum hight of the particle is determined by the above equation divided by two.

The monolayer on the metalized film contains a receptive material or binder, such as an antibody, that will specifically bind to an epitope on the analyte that is different from the epitope used in the binding to the particle. Thus, for detecting a medium with a small analyte, such as viral particles, the medium is first exposed to the latex particles to which the viral particles are bound. Then, the latex particles are optionally washed and exposed to the metalized film with the monolayers containing the virus specific antibodies. The antibodies then bind to the viral particles on the latex bead thereby immobilizing the latex beads in the same pattern as the monolayers on the film. Because the bound latex beads will cause diffraction of the visible light, a diffraction pattern is formed, indicating the presence of the viral particle in the liquid. Other combinations using particles are well known to those of ordinary skill in the art.

In another embodiment of the present invention, receptors, such as antibodies are attached to the metal layer as described herein. The antibodies are then exposed to an environment that contains analytes that bind to the receptor. After the analyte has bound to the receptor, a second receptor is added that recognizes the metal bound conjugate. To this second receptor is bound an enzyme or inorganic substance that will cause a precipitation of a solid substance when the appropriate reagent or reagents are added. For example, an enzyme that can cause a precipitate to form is peroxidase in the presence of tetramethylbenzidene (See Example 3 herein). Another example, is the use of colloidal gold in the presence of a silver halide. Elemental silver will precipitate on the patterned receptor layer thereby producing the diffraction pattern.

The analytes that are contemplated as being detected using the present invention include, but are not limited to, bacteria; yeasts; fungi; viruses; rheumatoid factor; antibodies, including, but not limited to IgG, IgM, IgA and IgE antibodies; carcinoembryonic antigen; streptococcus Group A antigen; viral antigens; antigens associated with autoimmune disease, allergens, tumor antigens; streptococcus Group B antigen, HIV I or HIV II antigen; or host response (antibodies) to these and other viruses; antigens specific to RSV or host response (antibodies) to the virus; antigen; enzyme; hormone; polysaccharide; protein; lipid; carbohydrate; drug or nucleic acid; Salmonella species; Candida species, including, but not limited to *Candida albicans* and *Candida tropicalis; Neisseria meningitides* groups A, B, C, Y and W sub 135, *Streptococcus pneumoniae, E. coli, Haemophilus influenza* type B; an antigen derived from microorganisms; a hapten; a drug of abuse; a therapeutic drug; an environmental agent; and antigens specific to Hepatitis.

In another embodiment of the present invention, nutrients for a specific class of microorganism can be incorporated into the monolayer. In this way, very low concentrations of microorganisms can be detected by first contacting the biosensor of the present invention with the nutrients incorporated therein and then incubating the biosensor under conditions appropriate for the growth of the bound microorganism. In one embodiment shown in FIG. 1, the MYLAR film 15 has a nutrient backing 30 that is in contact with the back of the MYLAR film 15. The opposite side of the MYLAR film 15 has a metal film 20 thereon. The metal film 20 is preferably gold. Attached to the metal film 20 are receptors 25 that are specific for a microorganism. In use, the nutrient diffuses slowly through the MYLAR film. When a microorganism is attached to receptor 25, the bound microorganism consumes the nutrient and grows. As the microorganism grows, it diffracts impinging light thereby forming a diffraction pattern. Thus, in this embodiment, if the diffraction pattern forms, it is because the bound microorganism grew. Of course, in some cases, the microorganism can multiply enough to form a diffraction pattern without the presence of a nutrient on the patterned monolayer.

A part of the present invention is a receptive material that can be microprinted on the metalized film and will specifically bind to the analyte of interest. Thus, the receptive material is defined as one part of a specific binding pair and includes, but is not limited to, antigen/antibody, enzyme/substrate, oligonucleotide/DNA, chelator/metal, enzyme/inhibitor, bacteria/receptor, virus/receptor, hormone/receptor, DNA/RNA, or RNA/RNA, oligonucleotide/RNA, and binding of these species to any other species, as well as the interaction of these species with inorganic species.

The receptive material that is bound to the attachment layer is characterized by an ability to specifically bind the analyte or analytes of interest. The variety of materials that can be used as receptive material is limited only by the types of material which will combine selectively (with respect to any chosen sample) with a secondary partner. Subclasses of materials which fall in the overall class of receptive materials include toxins, antibodies, antibody fragments, antigens, hormone receptors, parasites, cells, haptens, metabolites. allergens, nucleic acids, nuclear materials, autoantibodies, blood proteins, cellular debris, enzymes, tissue proteins. enzyme substrates, coenzymes. neuron transmitters, viruses, viral particles, microorganisms, proteins, polysaccharides, chelators, drugs, and any other member of a specific binding pair. This list only incorporates some of the many different materials that can be coated onto the attachment layer to produce a thin film assay system. Whatever the selected analyte of interest is, the receptive material is designed to bind specifically with the analyte of interest.

The matrix containing the analyte of interest may be a liquid, a solid, or a gas, and can include a bodily fluid such as mucous, saliva, urine, fecal material, tissue, marrow, cerebral spinal fluid, serum, plasma, whole blood, sputum, buffered solutions, extracted solutions, semen, vaginal secretions, pericardial, gastric, peritoneal, pleural, or other washes and the like. The analyte of interest may be an antigen, an antibody, an enzyme, a DNA fragment, an intact gene, a RNA fragment, a small molecule, a metal, a toxin, an environmental agent, a nucleic acid, a cytoplasm component, pili or flagella component, protein, polysaccharide, drug, or any other material, such as those listed in Table A. For example, receptive material for bacteria may specifically bind a surface membrane component, protein or lipid, a polysaccharide, a nucleic acid, or an enzyme. The analyte which is specific to the bacteria may be a polysaccharide, an enzyme, a nucleic acid, a membrane component, or an antibody produced by the host in response to the bacteria. The presence of the analyte may indicate an infectious disease (bacterial or viral), cancer or other metabolic disorder or condition. The presence of the analyte may be an indication of food poisoning or other toxic exposure. The analyte may indicate drug abuse or may monitor levels of therapeutic agents.

One of the most commonly encountered assay protocols for which this technology can be utilized is an immunoassay. However, the general considerations apply to nucleic acid probes, enzyme/substrate, and other ligand/receptor assay formats. For immunoassays, an antibody may serve as the receptive material or it may be the analyte of interest. The receptive material, for example an antibody or an antigen, must form a stable, dense, reactive layer on the attachment layer of the test device. If an antigen is to be detected and an antibody is the receptive material, the antibody must be specific to the antigen of interest; and the antibody (receptive material) must bind the antigen (analyte) with sufficient avidity that the antigen is retained at the test surface. In some cases, the analyte may not simply bind the receptive material, but may cause a detectable modification of the receptive material to occur. This interaction could cause an increase in mass at the test surface or a decrease in the amount of receptive material on the test surface. An example of the latter is the interaction of a degradative enzyme or material with a specific, immobilized substrate. In this case, one would see a diffraction pattern before interaction with the analyte of interest, but the diffraction pattern would disappear if the analyte were present. The specific mechanism through which binding, hybridization, or interaction of the analyte with the receptive material occurs is not important to this invention, but may impact the reaction conditions used in the final assay protocol.

In general, the receptive material may be passively adhered to the attachment layer in a pattern that will produce a diffraction pattern. If required, the free functional groups introduced onto the test surface by the attachment layer may be used for covalent attachment of receptive material to the test surface. Chemistries available for attachment of receptive materials are well known to those skilled in the art.

A wide range of techniques can be used to adhere the receptive material to the attachment layer in a pattern that, when bound to the analyte of interest, forms a diffraction pattern when light is transmitted through attachment layer. Test surfaces may be coated with receptive material by application of solution in discrete arrays or patterns; spraying, ink jet, or other imprinting methods; or by spin coating from an appropriate solvent system. The technique selected should minimize the amount of receptive material required for coating a large number of test surfaces and maintain the stability/functionality of receptive material during application. The technique must also apply or adhere the receptive material to the attachment layer in a very uniform and reproducible fashion.

The receptor layer is formed from material selected from the group consisting of antigens, antibodies, oligonucleotides, chelators, enzymes, bacteria, bacterial pili, bacterial flagellar materials, nucleic acids, polysaccharides, lipids, proteins, carbohydrates, metals, viruses, hormones and receptors for said materials In the preferred embodiments, the biosensing device is configured and arranged to provide a pattern detectable by eye in response to transmission of polychromatic light when the analyte of interest is sandwiched between the receptive material and a secondary binding reagent.

The medium in which the analyte may reside can be solid, gel-like, liquid or gas. For purposes of detecting an analyte in a body fluid, the fluid is selected from the group consisting of urine, serum, plasma, spinal fluid, sputum, whole blood, saliva, uro-genital secretions, fecal extracts, pericardial, gastric, peritoneal, pleural washes, vaginal secretions, and a throat swab; and the method optionally includes using a diffractometer to measure the appearance of the diffraction pattern. The most common gas that is contemplated as being used with the biosensing device of the present invention is air.

The biosensing device of the present invention utilizes methods of contact printing of patterned monolayers on metalized polymer films, desirably thermoplastic polymer films, the compositions produced thereby, and the use of these compositions. Patterned monolayers allow for the controlled placement of fluids thereon which can contain a analyte receptor. The term "patterned monolayers thereon" as used herein means the monolayers in any pattern on the metalized polymer films including a solid pattern.

When the film with the monolayers thereon is exposed to an analyte that is capable of reacting with the monolayer, the film will produce optical diffraction patterns which differ depending on the reaction of the monolayer with the analyte of interest. The liquid may be a high surface tension fluid such as water. The light can be in the visible spectrum, and be either reflected from the film, or transmitted through it, and the analyte can be any compound reacting with the monolayer.

In preferred embodiments, the method involves contacting the substrate with a test sample potentially containing the analyte under conditions in which the substrate causes a change in the refractive index of the monolayer. When light is transmitted through the metalized thermoplastic polymer with the monolayer, a visible pattern is formed and can be visualized by directing the light to a surface or by looking directly through the substrate.

In one embodiment, the present invention is contemplated in a dipstick form in which the micro-contact printed metalized film is mounted at the end of the dipstick. In use the dipstick is dipped into the liquid in which the suspected analyte may be present and allowed to remain for several minutes. The dipstick is then removed and then, either a light is projected through the metalized film or the film is observed with a light behind the film. If a pattern is observed, then the analyte is present in the liquid.

Figure 2:
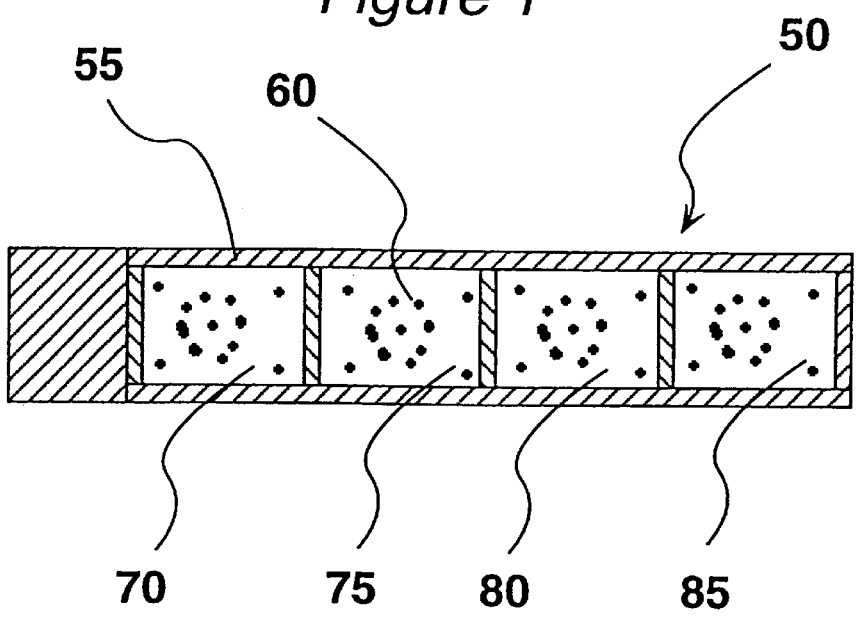
FIG. 2 shows a biosensor capable of simultaneously measuring several different analytes in a medium.

In another embodiment of the present invention, a multiple analyte test is constructed on the same support. As shown in FIG. 2, a strip 50 is provided with several micro-contact printed metalized films 70, 75, 80 and 85, each film having a monolayer pattern 60 printed thereon. Each of the micro-contact printed metalized films 70, 75, 80 and 85 have a different receptive material that is different for different analytes. It can be seen that the present invention can be formatted in any array with a variety of micro-contact printed metalized films thereby allowing the user of the biosensor device of the present invention to detect the presence of multiple analytes in a medium using a single test.

In yet another embodiment of the present invention, the biosensor can be attached to an adhesively backed sticker or decal which can then be placed on a hard surface or container wall. The biosensor can be placed on the inside surface of a container such as a food package or a glass vial. The biosensor can then be visualized to determine whether there is microbial contamination.

In one embodiment of the present invention, the receptor layer has the following general formula:

X is reactive with metal or metal oxide. For example, X may be asymmetrical or symmetrical disulfide (—R'SSR, —RSSR), sulfide (—R'SR, —RSR), diselenide (—R'Se—SeR), selenide (—R'SeR, —RSeR), thiol (—SH), nitrile (—CN), isonitrile, nitro (—$NO_2$), selenol (—SeH), trivalent phosphorous compounds, isothiocyanate, xanthate, thiocarbamate, phosphine, thioacid or dithioacid, carboxylic acids, hydroxylic acids, and hydroxamic acids.

R is an linker which may optionally be interrupted by hetero atoms and which are preferably non-branched for the sake of optimum dense packing. The linker, helps prevent steric hindrance and/or enhance activity of Y.

Y is the molecule that imparts functionality of the receptor layer. Y can be any molecule that preferentially binds the analyte of interest. Y can be toxins, antibodies, antibody fragments antigens, hormone receptors, parasites, cells, haptens, metabolizes. allergens, nucleic acids, nuclear materials, autoantibodies, blood proteins, cellular debris, enzymes, tissue proteins. enzyme substrates, coenzymes.

neuron transmitters, viruses, viral particles, microorganisms, proteins, polysaccharides, chelators, drugs, and any other member of a specific binding pair.

A desired reagent that can be reacted with potential binders such as antibodies or antibody fragments to provide functionality X, include, but are not limited to, sulfo-LC-SPDP (Pierce Chemical Co. Rockford, Ill.) which has the following formula:

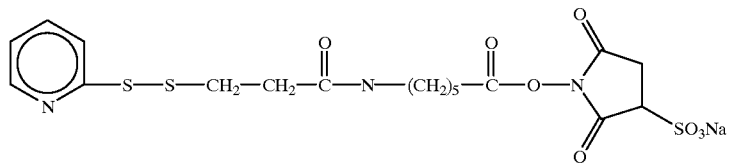

The sulfo-LC-SPDP is reactive towards sulfhydryl and amino groups and is therefore ideally suited for reaction with proteins such as antibodies or other protein receptors, proteoglycans, lipoproteins, glycoproteins, or amino sugars including, but not limited to, glucosamine or galactosamine.

Figure 3:
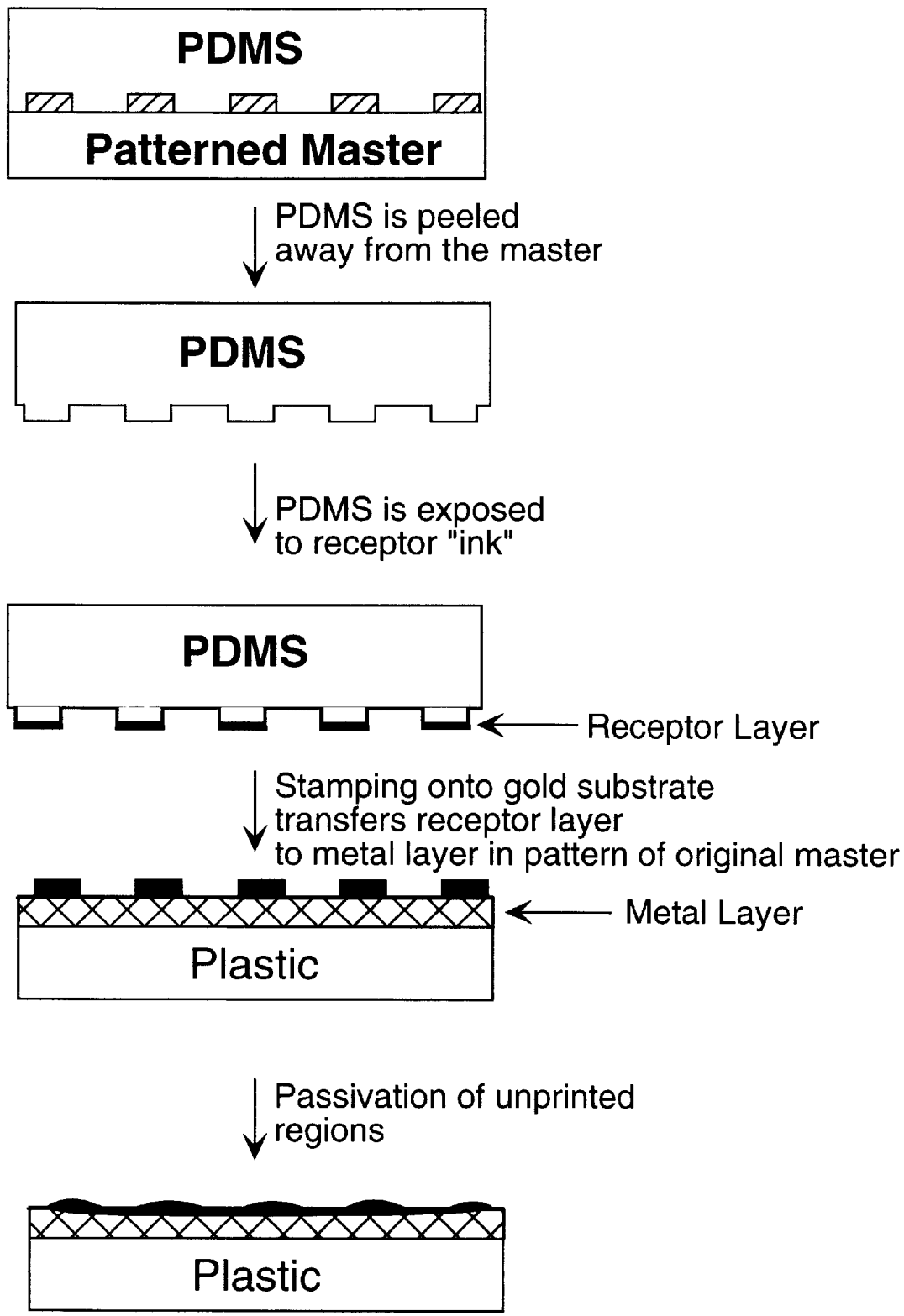
FIG. 3 is a schematic of contact printing of receptors according to the present invention.

In a typical experimental procedure, schematically shown in FIG. 3, a photolithographically produced master is placed in a glass or plastic Petri dish, and a 10:1 ratio (w:w or v:v) mixture or SYLGARD® silicone elastomer 184 and SYLGARD® silicone elastomer 184 curing agent (Dow Corning Corporation) is poured over it. The elastomer is allowed to sit for approximately 30 minutes at room temperature and reduced pressure to degas, then cured for 4 to 16 hours at 60° C., and gently peeled from the master.

"Inking " of the elastomeric stamp is accomplished by soaking the elastomeric stamp in an approximately 0.1 mG/mL to approximately 0.5 mG/mL concentration of the receptor "ink" for between approximately 10 seconds to 10 minutes, followed by drying the stamp under nitrogen gas. The stamp is allowed to dry until no liquid is visible by eye on the surface of the stamp (typically about 60 seconds), either under ambient conditions, or by exposure to a stream of nitrogen gas. Following inking, the stamp is applied (typically by hand) to a metalized surface. Very light hand pressure is used to aid in complete contact between the stamp and the surface. The stamp should desirably remain on the surface for between approximately 10 seconds to approximately 200 seconds. The actual time the stamp should remain on the surface will vary depending upon the ink used. The stamp is then gently peeled from the surface. A preferred embodiment will follow receptor printing with a passivation step to cover all the surface area of the metal not containing bound receptor. Passivation helps eleminate non-specfic binding of analyte.

The elastomeric character of the stamp is important to the success of the process. Polydimethylsiloxane (PDMS), when cured, is sufficiently elastomeric to allow good conformal contact of the stamp and the surface, even for surfaces with significant relief; this contact is essential for efficient contact transfer of the receptor "ink" to the gold film. The elastomeric properties of PDMS are also important when the stamp is removed from the master: if the stamp were rigid (as is the master) it would be difficult to separate the stamp and master after curing without damaging one of the two substrates. PDMS is also sufficiently rigid to retain its shape, even for features with sub-micron dimensions. Patterns have been successfully generated with lines as small as 200 nm in width. The surface of PDMS has a low interfacial free energy (y=22.1 dynes/cm), and the stamp does not adhere strongly to the metalized film. The stamp is durable in that the same stamp can be used up to 100 times over a period of several months without significant degradation in performance. The polymeric nature of PDMS also plays a critical role in the inking procedure, by enabling the stamp to absorb the alkanethiol ink without significant swelling. The stamp can be produced on a printing roll to allow for a continuous printing operation.

A more detailed description of the methods and compositions of the present invention follows. All publications cited herein are incorporated by reference in their entirety.

Any thermoplastic film upon which a metal substrate can be deposited is suitable for the present invention. These include, but are not limited to, polymers such as: polyethylene-terephthalate (MYLAR®), acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene—vinyl acetate copolymers, ionomers (ethylene polymers) polyethylene-nylon copolymers, polypropylene, methyl pentene polymers, polyvinyl fluoride, and aromatic polysulfones. Preferably, the plastic film has an optical transparency of greater than 80%. Other suitable thermoplastics and suppliers may be found, for example, in reference works such as the *Modern Plastics Encyclopedia* (McGraw-Hill Publishing Co., New York 1923–1996).

In one embodiment of the invention, the thermoplastic film with the metal coating thereon has an optical transparency of between approximately 5% and 95%. A more desired optical transparency for the thermoplastic film used in the present invention is between approximately 20% and 80%. In a desired embodiment of the present invention, the thermoplastic film has at least an approximately 80% optical transparency, and the thickness of the metal coating is such as to maintain an optical transparency greater than about 20%, so that diffraction patterns can be produced by either reflected or transmitted light. This corresponds to a metal coating thickness of about 20 nm. However, in other embodiments of the invention, the gold thickness may be between approximately 1 nm and 1000 nm.

The preferred metal for deposition on the film is gold. However, silver, aluminum, chromium, copper, iron, zirconium, platinum and nickel, as well as oxides of these metals, may be used. Chromium oxide can be used to make metalized layers.

In principle, any surface with corrugations of appropriate size could be used as masters. The process of microcontact printing starts with an appropriate relief structure, from which an elastomeric stamp is cast. This 'master' template may be generated photolithographically, or by other procedures, such as commercially available diffraction gratings. In one embodiment, the stamp may be made from polydimethylsiloxane.

In one embodiment, the present invention features an optical assay device, having an optically active receptive surface configured and arranged to allow simultaneous assay of a plurality of samples on the surface for one analyte of interest, and an automated liquid handling apparatus (e.g., a pipetting device) configured and arranged to dispense sample and reagent solutions to the surface.

The present invention has a broad range of applications and, may be utilized in a variety of specific binding pair assay methods. For example, the devices of this invention can be used in immunoassay methods for either antigen or antibody detection. The devices may be adapted for use in direct, indirect, or competitive detection schemes, for determination of enzymatic activity, and for detection of small organic molecules (e.g., drugs of abuse, therapeutic drugs, environmental agents), as well as detection of nucleic acids.

The stamp may be applied in air, or under a fluid such as water to prevent excess diffusion of the alkanethiol. For large-scale or continuous printing processes, it is most desirable to print in air, because shorter contact times are desirable for those processes.

In one embodiment of the present invention, the pattern is formed on the metalized thermoplastic polymer with the receptor layer. In another embodiment of the present invention, the relief of the pattern is formed with the receptor layer. After the stamping process, the metalized areas on the plastic may optionally be passivated, for example, with a methyl-terminated monolayer such as hexadecylmercaptan.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

An example derivatization of an antibody to *E. coli* 0157:H7 (Kirkegaard & Perry Labs) follows: To 1 mG of antibody was added 450 $\mu$L phosphate buffered saline (PBS) and 50 $\mu$L of a 10 mM aqueous solution of Sulfo-LC-SPDP (Pierce Catalog #21650). After 60 minutes at room temperature, the solution is desalted in a D-Salt™ Polyacrylamide desalting column (Pierce, Rockford, Ill.) An acetate buffer, pH 4.5 was used if a subsequent reduction of the disulfide bond was done, while a PBS buffer, pH 7.5, was used if the antibody derivative was to remain as the disulfide. 500 $\mu$L fractions were collected from the column, and the fraction with antibody derivative was determined using a Coomassie® Plus Protein Assay.

EXAMPLE 2

The resulting thiolated antibody from Example 1, either disulfide or thiol, is contact printed on gold-coated MYLAR®. The elastomeric stamp is soaked in a 0.5 mG/mL concentration of the thiolated antibody for 10 minutes, followed by drying the stamp under nitrogen gas, and then contacted with a gold-coated MYLAR® film for 10–120 seconds.

EXAMPLE 3

Figure 4:
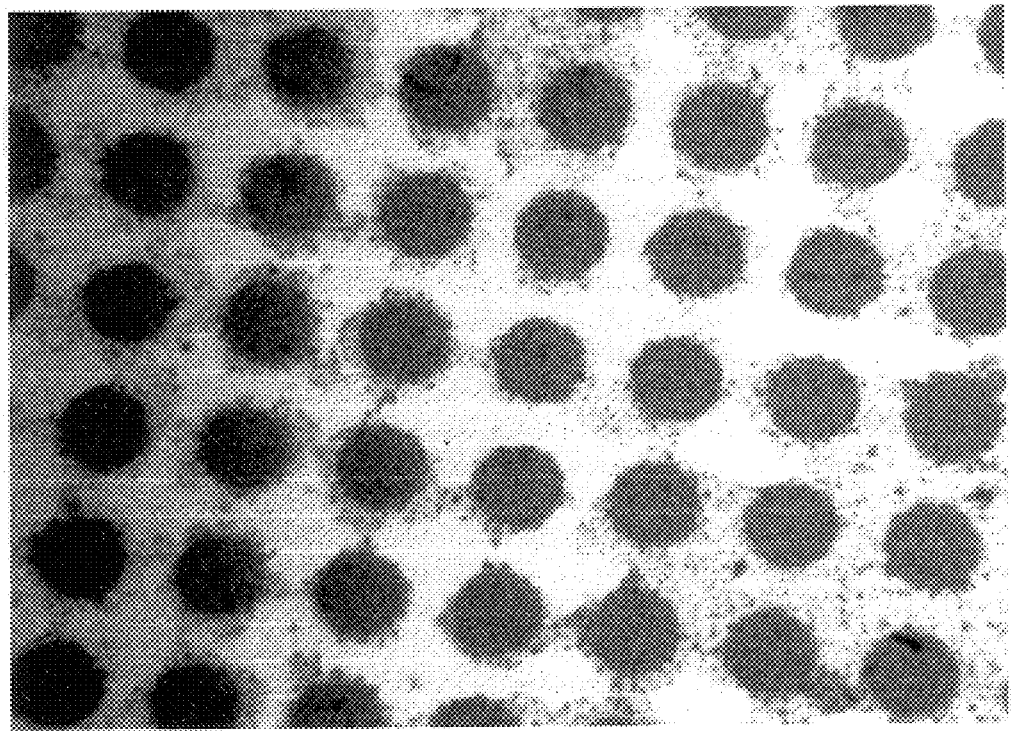
FIG. 4 is an enzyme-linked immunosorbent assay (ELISA) of the surface printed with a thiolated antibody binder.
Figure 6:
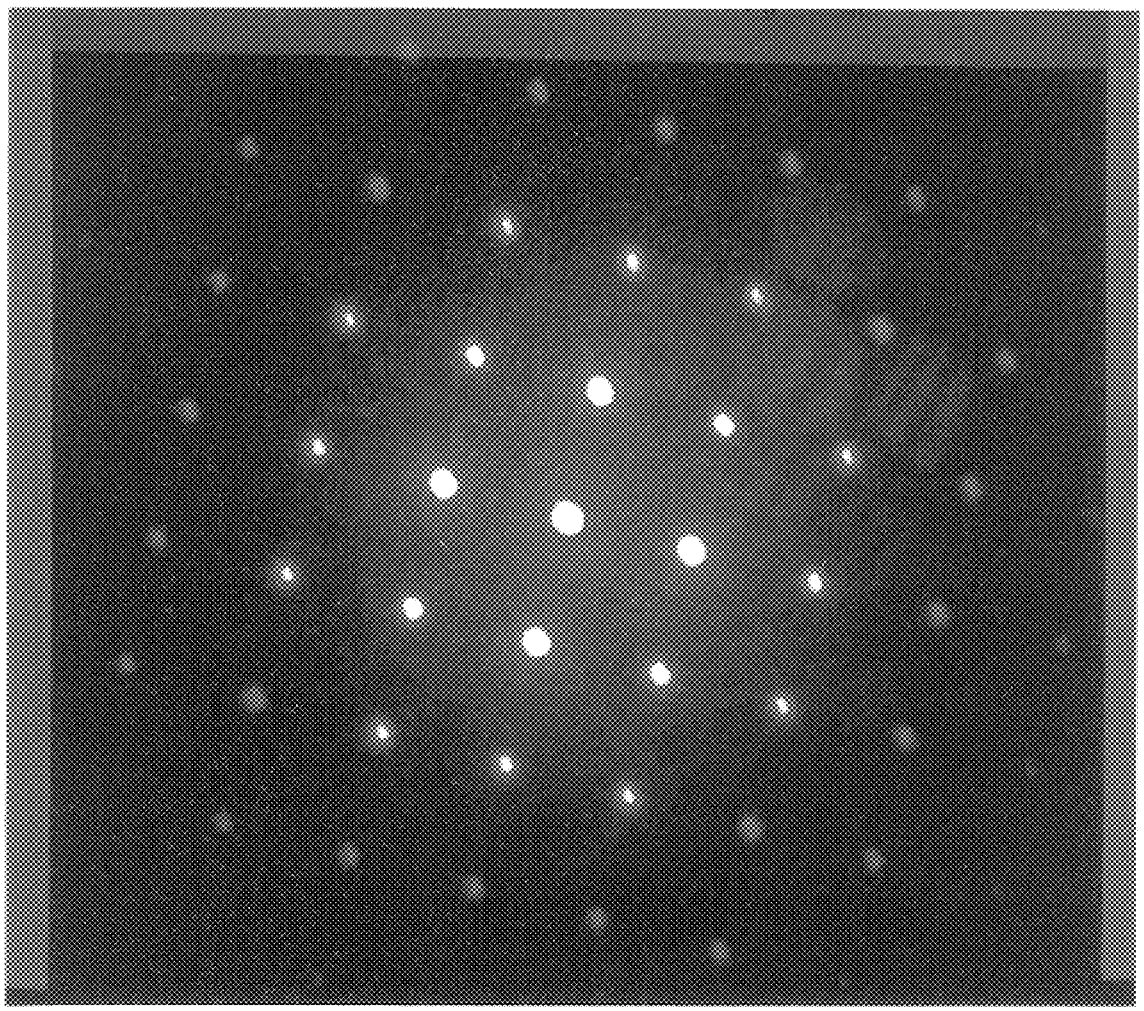
FIG. 6 is a diffraction pattern produced from the sample described in FIG. 4.

In this example, a condensation figure is produced. The non-patterned areas after printing as described in Example 2 are reacted with another thiol, such as hexadecanethiol. The condensation figure remained, indicating that the thiolated antibody is chemisorbed and not displaced. An enzyme-linked immunosorbent assay (ELISA) of the printed surface was positive in the patterned areas, verifying the presence of active antibody in the pattern (FIG. 4). The ELISA utilized a peroxidase conjugated with an antibody specific for the *E. coli* antibody used in Example 1. Tetramethylbenzidene precipitation on the patterned antibody sandwich produced the diffraction pattern. Polystyrene surrogate particles surface modified with antigen also produced patterned adsorption to the receptor layer. The diffraction pattern produced by the tetramethylbenzidene precipitation is shown in FIG. 6.

EXAMPLE 4

Figure 5:
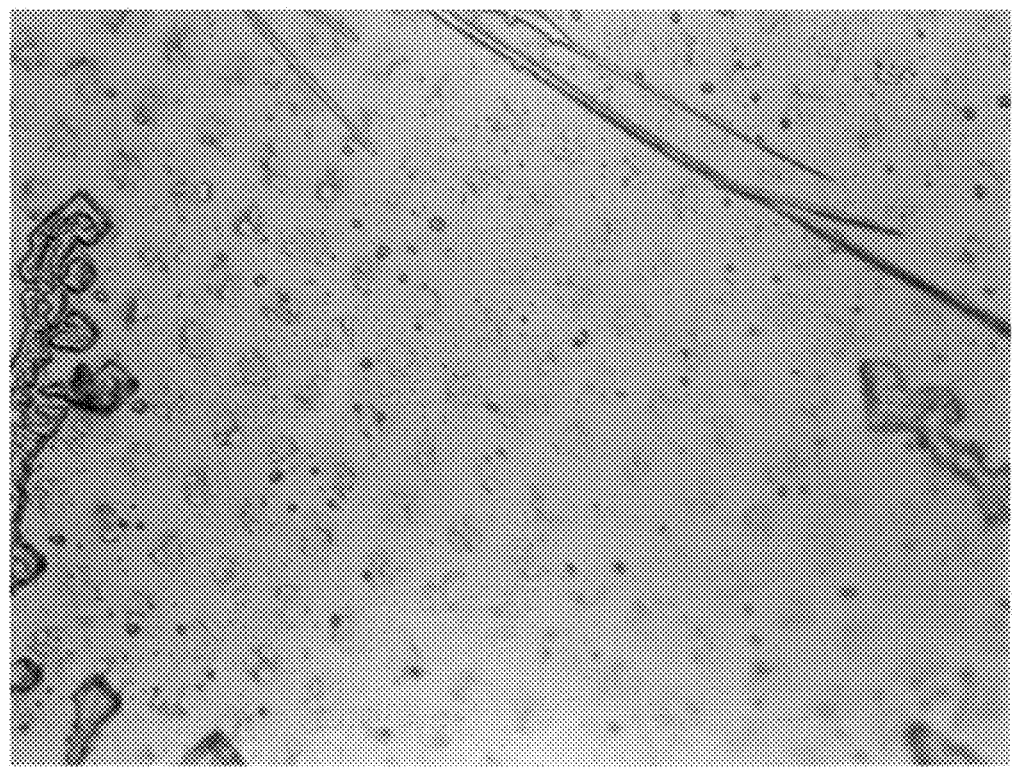
FIG. 5 is a photograph showing polystyrene surrogate particles coated with antigen after attachment to the printed antibody.

A surrogate polystyrene particle was produced by carbodiimide coupling with ethyldimethylaminodicarbodiimide (EDAC-Sigma Chemical Company, St. Louis, Mo.) of *E. coli* 0157:H7 antigen(Kirkegaard & Perry Labs, Cat# 50-95-90) to one micron polystyrene latex spheres by conventional techniques. A 2 wt % solution of the diimide was reacted with carboxylate modified PS latex(Bangs: $10^{10}$ particles/mL) for 4 hours, followed by exposing these activated particles to a 400 uG/mL solution of antigen. This surrogate, diluted to $10^8$ particles/mL, was exposed to a sensor containing patterned antibody to *E. Coli* 0157:H7, produced as described in Example 2, for 60 minutes. After washing with phosphate buffer, the sample was dried, photographed (FIG. 5) and was shown to produce a diffraction pattern as described in Example 3.

EXAMPLE 5

It is well established that one criteria for the presence of a self assembling monolayer (SAM) is increased resistance to chemical etchants and that alkane thiol self assembled monolayers provide resistance of gold to cyanide etching. Cyanide etching was performed to determine if the thiolated protein or oligonucleotide binders of this invention form a protective SAM on gold. Gold coated polyester film (35 nM gold thickness) was exposed to aqueous solutions of either a thiolated antibody to *Candida albicans* (0.5 mG/mL), thiolated protein G (0.5 mG/mL), thiolated oligonucleotide (10 $\mu$M), or underivatized antibody to *Candida albicans* (physisorption only; 0.5 mG/mL); an ethanol solution of hexadecane thiol (HDT; 5.7 mM), known to form a SAM on gold, was used as a positive control. After 16 hours exposure to the thiol containing binders, the coated gold samples were removed, thoroughly rinsed with solvent (water or ethanol), and dried under a nitrogen stream.

Binder coated samples were immersed in an aqueous solution of potassium cyanide (100 mM) containing potassium hydroxide (0.5 M) while bubbling air (oxygen) into the solution. After etching for 11 minutes, the samples were removed, rinsed with water, and visually evaluated for the amount of gold remaining. Table 1 summarizes the observations. The HDT sample was the only sample with most of the gold remaining on its surface. The thiolated antibody had a very small amount of gold ($\approx$5% coverage), while the other samples had no gold remaining after etching. This demonstrates that unlike HDT, the thiolated binders used to prepare the optical diffraction biosensors do not form a protective SAM.

TABLE 1

Summary of Cyanide Etching Experiments

| Sample | Observations after etching |
| --- | --- |
| Hexadecane thiol (HDT) | 70–80% |
| Thiolated Antibody | ~5% (random specks) |
| Antibody (physisorbed on surface) | no gold remaining |
| Thiolated Protein G | no gold remaining |
| Thiolated Oligonucleotide | no gold remaining |

EXAMPLE 6

Samples with patterned antibody to *Candida albicans* were prepared as follows: Gold/polyester(10 nM gold thickness) was pre-treated by immersing it in a 5 mG/mL phosphate-buffered saline solution (pH 7.2) of beta casein (Sigma catalog # C6905) for 10 minutes. The sample was thoroughly rinsed with distilled water, and dried under a strong nitrogen stream. Contact printing was done using a polydimethyl siloxane stamp having an x,y array of 10-micron diameter circles. The stamp was coated with a thiolated antibody to *Candida albicans* (initial polyclonal antibody was Catalog # 20-CRO4 from Fitzgerald Industries International, Inc., Concord, Mass.) by immersing the stamp in a 0.5 mG/mL aqueous solution of the antibody derivative. After 10 minutes, the stamp was removed and thoroughly dried using a strong stream of nitrogen. Contact printing was done on the casein-treated sample, with exposure times of 1 second to 2 minutes being adequate. Two minutes was the preferred contact time. After printing, the sample was again rinsed with distilled water and dried.

Figure 7:
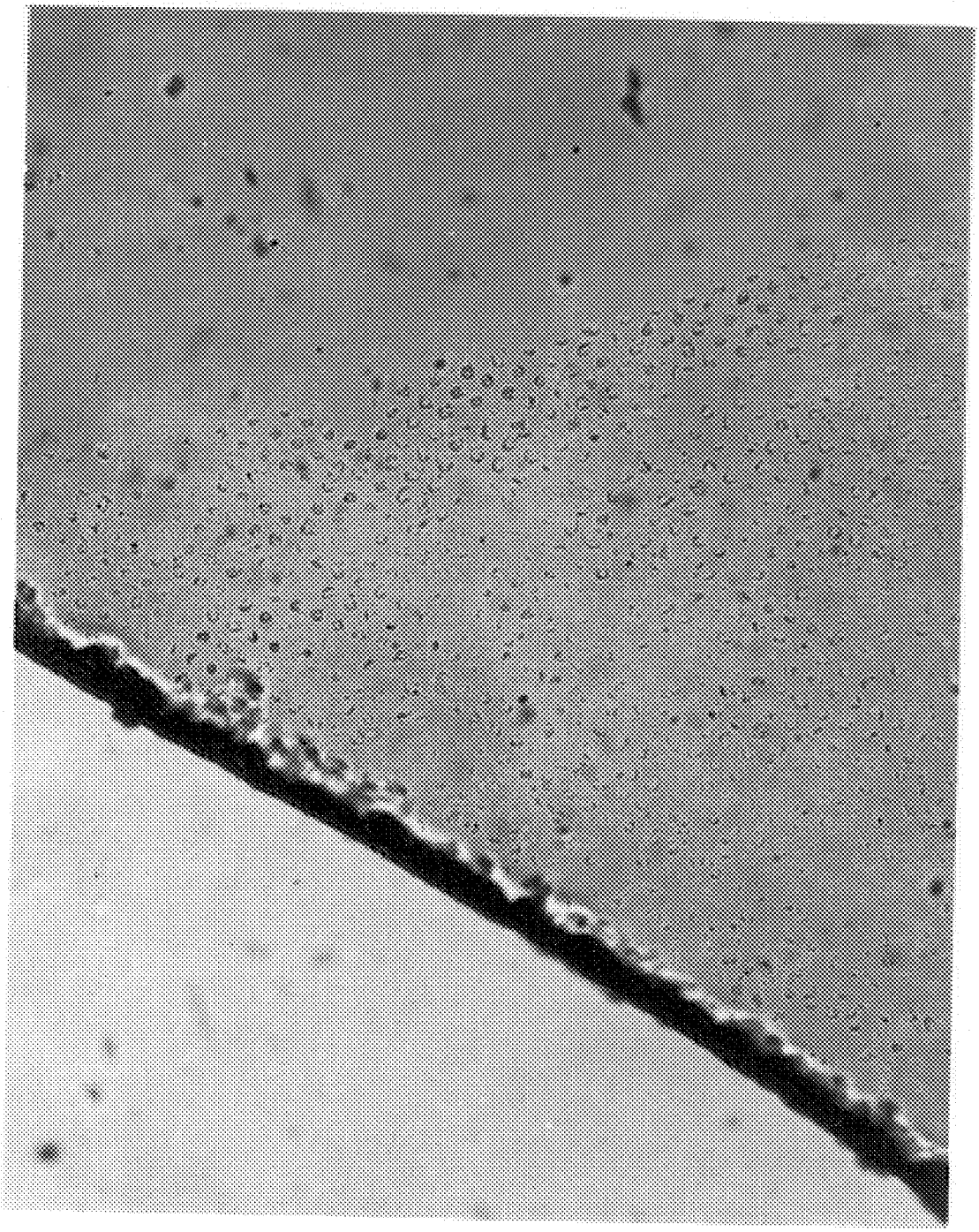
FIG. 7 is an optical photomicrograph of *Candida albicans* attached to a patterned antibody receptor.
Figure 8:
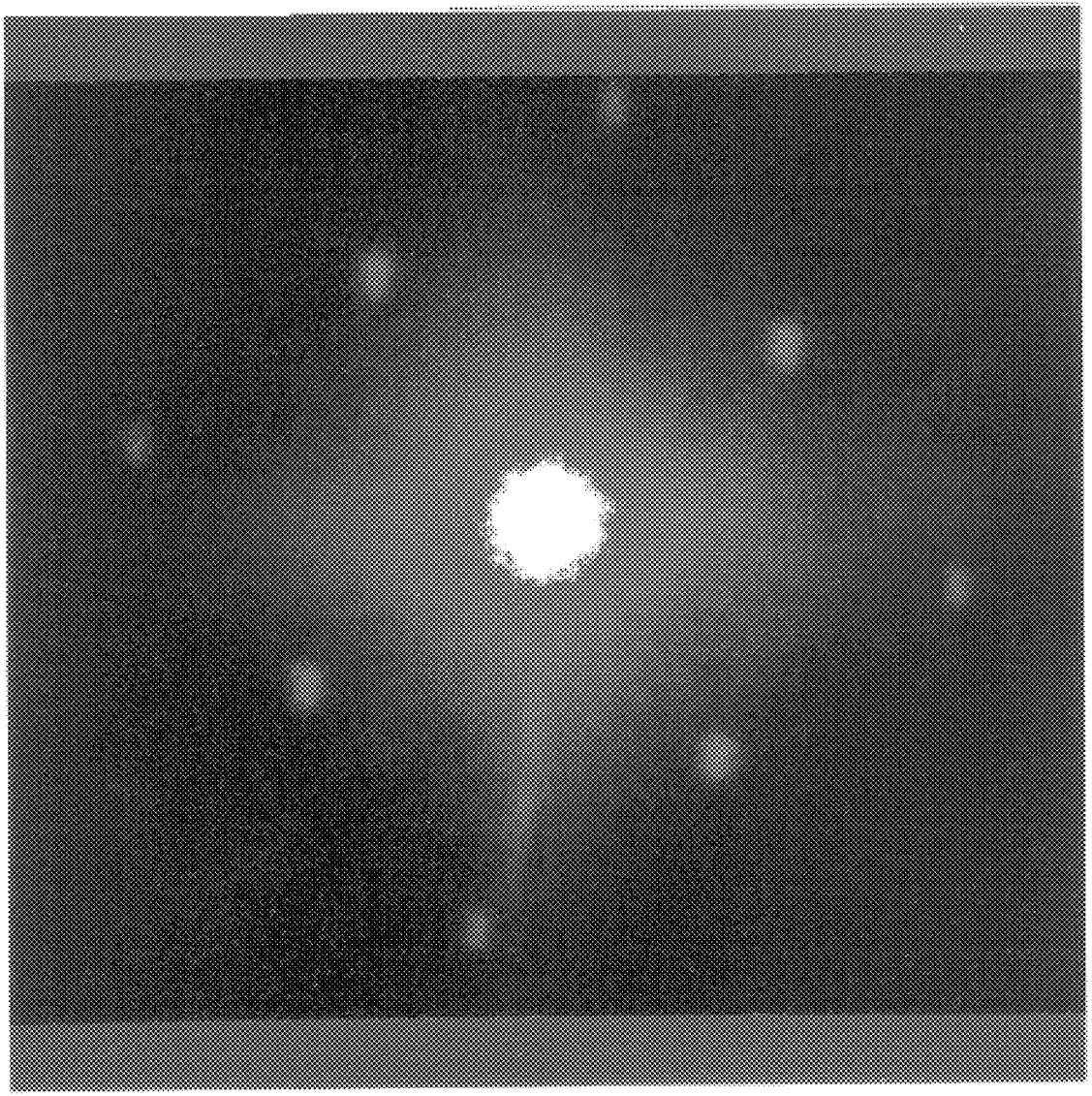
FIG. 8 is a diffraction pattern caused by the binding of *Candida albicans* to the patterned receptor.

The sensor sample was exposed to germ tube-bearing cells of *Candida albicans* by inoculating tape-stripped adult forearm skin with a concentration of $10^6$ yeast cells per milliliter, and placing the sensor on top of the yeast containing tape. Transfer of the yeast cells to the sensor was accomplished after only a few seconds of contact (FIG. 7). Patterned adhesion of the yeast cells to the sensor was confirmed by microscopic analysis, and resulted in a diffraction image upon irradiation with a laser (FIG. 8).

Other surfaces which have been inoculated with germ tube-bearing cells of *Candida albicans* have been an agar plate and a HUGGIES® Baby Wipe. Exposure of these surfaces to the antibody-based sensors has also resulted in patterned attachment of the cells, and diffraction images.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

We claim:

1. A biosensor comprising:
    a polymer film coated with metal; and
    a patterned receptor layer printed onto the polymer film wherein the receptor layer has a receptive material thereon that specifically binds an analyte;
    wherein the receptor layer is printed in a pattern such that when the biosensor binds an analyte, the biosensor diffracts transmitted light or reflected light to form a diffraction pattern visible to an unaided eye.

2. The biosensor of claim 1, wherein the diffraction pattern forms a hologram.

3. The biosensor of claim 1, wherein the metal is gold, silver, chromium, nickel, platinum, aluminum, iron, copper, chromium oxide or zirconium.

4. The biosensor of claim 3, wherein the metal is gold.

5. The biosensor of claim 3, wherein the metal coating is between approximately 1 nanometer and 1000 nanometers in thickness.

6. The biosensor of claim 1, wherein the polymer film is polyethylene-terephthalate, acrylonitrile-butadiene-styrene, acrylonitrile-methyl acetate copolymer, cellophane, ethyl cellulose, cellulose acetate, cellulose acetate butyrate, cellulose propionate, cellulose triacetate, polyethylene, polyethylene-vinyl acetate copolymers, ionomers (ethylene polymers) polyethylene-nylon copolymers, polypropylene, methyl pentene polymers, polyvinyl fluoride, or aromatic polysulfones.

7. The biosensor of claim 6, wherein the polymer film is polyethylene-terephthalate.

8. The biosensor of claim 1, wherein the polymer film is optically transparent.

9. The biosensor of claim 1, wherein the polymer film has an optical transparency between 5% and 95%.

10. The biosensor of claim 1, wherein the polymer film has an optical transparency between approximately 20% and 80%.

11. The biosensor of claim 1, wherein the patterned receptor layer is formed from compounds with the following general formula:

X—R—Y wherein:
    X is reactive with the metal or metal oxide on the polymer film;
    R is an optional linker; and
    Y is a compound with any property of interest.

12. The biosensor of claim 11, wherein R is between 0 and 12 carbon atoms in length.

13. The biosensor of claim 11, wherein X is generated from a compound comprising the following formula:

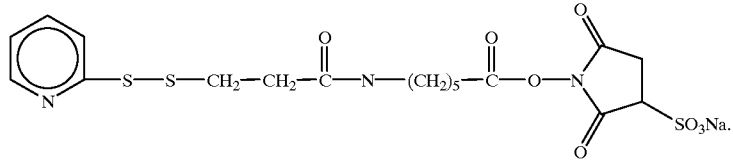

14. The biosensor of claim 1, wherein the analyte is bacteria, yeast, fungus, virus, rheumatoid factor, IgG, IgM, IgA and IgE antibodies, carcinoembryonic antigen, streptococcus Group A antigen, viral antigens, antigens associated with autoimmune disease, allergens, tumor antigens, streptococcus Group B antigen, HIV I or HIV II antigen, antibodies viruses, antigens specific to RSV, an antibody, antigen, enzyme, hormone, polysaccharide, protein, lipid, carbohydrate, drug, nucleic acid, *Neisseria meningitides* groups A, B, C, Y and W sub 135, *Streptococcus pneumoniae, E. coli* K1, *Haemophilus influenza* type B, an antigen derived from microorganisms, a hapten, a drug of abuse, a therapeutic drug, an environmental agents, or antigens specific to Hepatitis.

15. The biosensor of claim 14, wherein the analyte is bacteria, yeast, fungus or virus.

16. The biosensor of claim 1, wherein the receptor material is antigens, antibodies, nucleotides, chelators, enzymes, bacteria, yeasts, fungi, viruses, bacterial pili, bacterial flagellar materials, nucleic acids, polysaccharides, lipids, proteins, carbohydrates, metals, hormones and receptors for said materials.

17. The biosensor of claim 16, wherein the fungus is Candida species.

18. The biosensor of claim 16, wherein the bacteria is Salmonella species.

19. The biosensor of claim 1, wherein the biosensor is attached to the inside wall of a container.

20. The biosensor of claim 19, wherein the container is a vial.

21. The biosensor of claim 18, wherein the container is a food container.

22. The biosensor of claim 1, wherein the biosensor is attached to the inside wall of a garment.

23. The biosensor of claim 21, wherein the garment is a diaper.

24. The biosensor of claim 1, wherein the analyte is attached to a particle.

25. The biosensor of claim 24, wherein the particle is comprised of glass, cellulose, latex, polystyrene, polycarbonate, protein, or microbial cells.

26. The biosensor of claim 24, wherein the particle is between approximately 0.2 nm and 50 nm.

27. The biosensor of claim 26, wherein the particle is between approximately 0.4 $\mu$m to 1 $\mu$m.

28. The biosensor of claim 26, wherein the particle size is determined by the following formula:

$$t_{opt} = \lambda/2(n_2 - n_1)$$

wherein $t_{opt}$ = optimum height of the particle $\lambda$ = wavelength of incoming light $n_2$ = refractive index of particle $n_1$ = refractive index of surrounding medium.

29. A method of making a biosensor comprising applying a receptor layer to a polymer film coated with metal in a pattern such that when an analyte binds to the patterned receptor layer, the patterned receptor layer thereby forms a diffraction image visible to an unaided eye.

* * * * *